United States Patent [19]

Williams

[11] Patent Number: 5,098,909
[45] Date of Patent: Mar. 24, 1992

[54] 5-HT$_3$ RECEPTOR ANTAGONISTS FOR TREATMENT OF COUGH AND BRONCHOCONSTRICTION

[75] Inventor: Andrew J. Williams, Epsom, England

[73] Assignee: Beecham Group, p.l.c., Middlesex, England

[21] Appl. No.: 381,666

[22] PCT Filed: Nov. 14, 1988

[86] PCT No.: PCT/GB88/00994

§ 371 Date: Jul. 10, 1989

§ 102(e) Date: Jul. 10, 1989

[87] PCT Pub. No.: WO89/04660

PCT Pub. Date: Jun. 1, 1989

[30] Foreign Application Priority Data

Nov. 14, 1987 [GB] United Kingdom ............... 8726716
Nov. 14, 1987 [GB] United Kingdom ............... 8726717

[51] Int. Cl.$^5$ ........................................... A01N 93/42
[52] U.S. Cl. .................................. 514/286; 514/490; 514/849; 546/133; 546/63
[58] Field of Search ............... 546/133; 514/277, 849, 514/490, 286

[56] References Cited

FOREIGN PATENT DOCUMENTS 200444 11/1986 European Pat. Off. .

OTHER PUBLICATIONS

Chemical Abstracts, vol. 109, p. 696, 1988, 1902422.
Br. J. Pharmacol., vol. 87, No. 2, Feb. 1986, The Macmillan Press Ltd.; H. E. Connor et al.: "5-carboxamidotryptamine is a selective agonist at 5-hydroxytryptamine receptors mediating vasodilatation and tachycardia in anaesthetized cats", pp. 417-426, see the abstract.
J. Physiol. (London), vol. 365, 1985 (GB), D. J. Armstrong et al.: "MDL 72222 (a 5-HT abtagonist) antagonizes the pulmonary depressor and respiratory chemoreflexes evoked by phenylbiguanide in anaesthetized rabbits", p. 104P.
Chest, vol. 92, No. 5, Nov. 1987, M. Cazzola et al.: "Ketanserin, a new blocking agent of serotonin S$_2$-receptors. Respiratory functional effects in chronic obstruction of the airways", pp. 863-866, see the abstract.
Allgemeine und Spezielle Pharmakologie und Toxikologie, 3rd edition, Bibliographisches Institut, Mannheim (DE), 1980, p. 151.

Primary Examiner—José G. Dees
Assistant Examiner—Deborah D. Carr
Attorney, Agent, or Firm—Hopgood, Calimafde, Kalil, Blaustein & Judlowe

[57] ABSTRACT

A method of treatment of cough and/or bronchoconstriction in mammals, including humans, which method comprises the administration to the mammal in need of such treatment, an effective amount of a 5-HT$_3$ receptor antagonist.

8 Claims, No Drawings

5-HT₃ RECEPTOR ANTAGONISTS FOR TREATMENT OF COUGH AND BRONCHOCONSTRICTION

This invention relates to a method of treatment of cough and/or bronchoconstriction in mammals, including humans, and to the use of compounds in the preparation of a medicament for the treatment of cough and/or bronchoconstriction.

GB 2125398A, EP-A-200444, EP-A-247266, EP-A-235878, EP-A-67770, EP-A-158265, EP-A-158532 and EP-A-254584 disclose classes of compounds which are 5-HT₃ receptor antagonists, useful in the treatment of inter alia migraine, cluster headache and trigeminal neuralgia. GB 2153821A describes a further class of 5HT₃ receptor antagonists.

It has now been discovered that 5HT₃ receptor antagonists, such as certain of the above classes of compounds, are of potential use in the treatment of cough and/or bronchoconstriction, such as that arising as a result of asthma.

Cough is useful when it effectively expels secretions i.e. when it is a productive cough. Dry or unproductive cough has no useful effect. Unproductive cough may arise from effects such as cancer (primary or secondary) affecting sensory nerves in the larynx or larger bronchi, from asthma—especially childhood asthma—and in the early or later stages of coryza. Unproductive cough may also occur due to infiltration of the cough centre in the brain by tumour. Cough may also occur without known cause.

Treatment of cough by drugs is unsatisfactory.

Peripheral stimulation of sensory nerves in the larynx (which can cause cough) can be blocked by local anaesthetics such as lignocaine, but the only effective form of therapy for dry and painful cough used clinically is provided by the opiates (morphine, codiene, and methadone etc.).

Accordingly, the present invention provides a method of treatment of cough and/or bronchoconstriction in mammals, including humans, which method comprises the administration to the mammal in need of such treatment, an effective amount of a 5-HT₃ receptor antagonist, such as a compound of formula (I) or (II) or a pharmaceutically acceptable salt thereof:

$$X-CO-Y-Z \qquad (I)$$

wherein
X is a group of formula (a), (b), (c), (d) or (e):

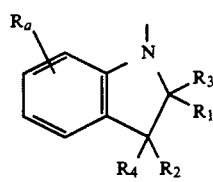
(a)

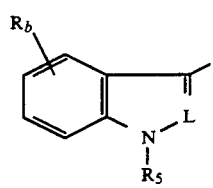
(b)

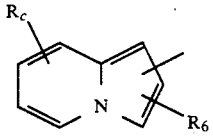
(c)

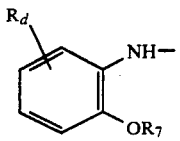
(d)

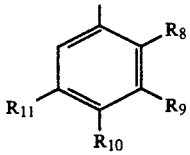
(e)

wherein
$R_a$ to $R_d$ are selected from hydrogen, halogen or hydroxy;
$R_1$ is hydrogen and $R_2$ is hydrogen or $C_{1-4}$ alkyl; or
$R_1$ and $R_2$ together are a bond;
$R_3$ to $R_7$ are independently hydrogen or $C_{1-6}$ alkyl; and
$R_4$ together with $R_2$ may be $C_{2-7}$ polymethylene when $R_1$ is hydrogen;
either $R_8$ is $C_{1-6}$ alkoxy;
$R_9$ is hydrogen;
$R_{10}$ is amino or $C_{1-7}$ alkanoylamino; and
$R_{11}$ is halo or $C_{1-6}$ alkylthio; or
$R_8$ is hydrogen;
$R_9$ is halo, $C_{1-6}$ alkoxy or $C_{1-6}$ alkyl;
$R_{10}$ is hydrogen or $C_{1-6}$ alkoxy; and
$R_{11}$ is halo, $C_{1-6}$ alkoxy or $C_{1-6}$ alkyl;
L is CH or N;
Y is NH or O, with the proviso that Y is NH when X is (e) and $R_8$ is $C_{1-6}$ alkoxy;
Z is a group of formula (f), (g) or (h):

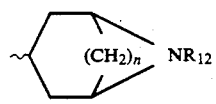
(f)

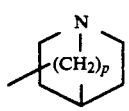
(g)

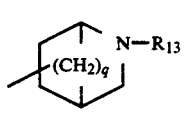
(h)

wherein
n is 2 or 3;
p and q are independently 1 to 3; and
$R_{12}$ or $R_{13}$ is methyl or ethyl;
and with the proviso that, when Ar is of formula (b) and Y is —NH—, Z is a group of formula (d) or (e);

wherein $R_{12}$ is hydrogen, $C_{1-10}$ alkyl, $C_{3-7}$ cycloalkyl, $C_{3-6}$ alkenyl, phenyl or phenyl-$C_{1-3}$ alkyl; and one of the groups represented by $R_{13}$, $R_{14}$ and $R_{15}$ is hydrogen, $C_{1-6}$ alkyl, $C_{3-7}$ cycloalkyl, $C_{2-6}$ alkenyl or phenyl-$C_{1-3}$ alkyl and each of the other groups, which may be the same or different, is hydrogen or $C_{1-6}$ alkyl.

In formula (I):

Examples of moieties in alkyl or alkyl containing groups in $R_1$ to $R_{11}$ include methyl, ethyl, n- and iso-propyl, n-, iso-, sec- and tert-butyl, preferably methyl.

Suitable examples of $R_2$ and $R_4$ when joined include $C_2$, $C_3$, $C_4$, $C_5$ or $C_6$ polymethylene, preferably $C_2$, $C_3$, $C_4$ or $C_5$ polymethylene.

$R_a$ to $R_d$ are preferably selected from hydrogen, fluoro, chloro and hydroxy, most preferably hydrogen. $R_b$ may be 5-, 6- or 7-chloro or fluoro.

When X is of sub-formula (a), $R_1$ and $R_3$ are preferably both hydrogen and one or both of $R_2$ and $R_4$ (most preferably both) are alkyl groups, such as methyl, or are joined to form $C_{2-7}$ polymethylene; or when one of $R_2$ and $R_4$ is hydrogen, the other is preferably ethyl or n- or iso- propyl.

When X is of sub-formula (b), $R_5$ is preferably hydrogen or a methyl or ethyl group.

When X is of sub-formula (c), one of CO—Y—Z and $R_6$ is attached at the 1-position and the other is attached at the 3-position as depicted in sub-formula (c), and $R_6$ is preferably methyl or ethyl.

When X is of sub-formula (d), $R_7$ is preferably methyl.

When X is of sub-formula (e), and $R_8$ is $C_{1-6}$ alkoxy, $R_8$ is preferably methoxy, $R_{10}$ is preferably amino and $R_{11}$ is preferably chloro or bromo, most preferably chloro.

When X is of sub-formula (e), and $R_8$ is hydrogen, $R_9$ and $R_{11}$ are preferably chloro or methyl and $R_{10}$ is preferably hydrogen.

X is preferably a group of formula (b) and L is preferably N.

Y is preferably NH.

When Z is a group of sub-formula (f), n is 2 or 3, preferably 3 when X is of sub-formula (b) wherein L is N.

When Z is a group of sub-formula (g) or (h), p and q are preferably 1 or 2.

In formula (II):

It will be understood that when $R_{12}$ represents a $C_{3-6}$ alkenyl group, the double bond may not be adjacent to the nitrogen atom.

The alkyl groups represented by $R_{12}$, $R_{13}$, $R_{14}$ and $R_{15}$ may be for example, methyl, ethyl, propyl, prop-2-yl, butyl, but-2-yl, methylprop-2-yl, pent-3-yl or hexyl.

An alkenyl group may be, for example, a propenyl group.

A phenyl-$C_{1-3}$ alkyl group may be for example, a benzyl, phenethyl or 3-phenylpropyl group. A cycloalkyl group may be, for example, a cyclopentyl, cyclohexyl or cycloheptyl group.

The pharmaceutically acceptable salts of the compounds of the formulae (I) and (II) include acid addition salts with conventional acids such as hydrochloric, hydrobromic, boric, phosphoric, sulphuric acids and pharmaceutically acceptable organic acids such as acetic, tartaric, lactic, maleic, citric, succinic, benzoic, ascorbic, methanesulphonic, α-keto glutaric, α-glycerophosphoric, and glucose-1-phosphoric acids.

The pharmaceutically acceptable salts of the compounds 5 of the formulae (I) and (II) are usually acid addition salts with acids such as hydrochloric, hydrobromic, phosphoric, sulphuric, citric, tartaric, lactic and acetic acid.

Preferably the acid addition salt is the hydrochloride salt.

Pharmaceutically acceptable salts also include quaternary derivatives, examples of which include the compounds quaternised by compounds such as $R_x$—T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide such as chloride, bromide and iodide.

Pharmaceutically acceptable salts also include internal salts such as pharmaceutically acceptable N-oxides.

The compounds of the formulae (I) and (II), and their pharmaceutically acceptable salts may also form pharmaceutically acceptable solvates, such as hydrates which are included wherever a compound of formula (I) or (II), or a salt thereof is herein referred to.

It will of course be realized that some of the compounds of the formulae (I) and (II) have chiral or prochiral centres, and thus are capable of existing in a number of stereoisomeric forms, including enantiomers. The invention extends to each of these stereoisomeric forms (including enantiomers), and to mixtures thereof (including racemates). The different stereoisomeric forms may be separated one from the other by the usual methods.

Compounds of the formulae (I) and (II) and their salts may be prepared in accordance with the methods described in the aforementioned Patent Publications. Examples of interest include the compounds within formulae (I) and (II) which are specific examples in the aforementioned patent publications. Particular examples include the following compounds:

i) The compound of Example 5 of EP-A-247266.

ii) The compound of Example 6 of EP-A-200444 (BRL 43694A).

iii) The compound of Example A-2 of GB 2125398A (ICS 205-930).

iv) The compound of Example 1 of EP-A-67770 (MDL 72222).

v) The compound of Example 1a of GB 2153821A (GR 38032F).

The administration of the 5-HT$_3$ receptor antagonist may be by way of oral or parenteral administration; or by inhalation.

An amount effective to treat the disorders hereinbefore described depends on the relative efficacies of the compounds of the invention, the nature and severity of the disorder being treated and the weight of the mammal. However, a unit dose for a 70 kg adult will normally contain 0.1 to 100 mg for example 0.2 to 50 mg, of the compound of formula (I) or (II) or a pharmaceutically acceptable salt thereof. Unit doses may be administered once or more than once a day, for example, 2, 3 or 4 times a day, more usually 1 to 3 times a day, that is in the range of approximately 0.0002 to 5 mg/kg/day, more usually 0.0004 to 2.5 mg/kg/day. In the case of the preferred compounds of the invention, the dose range is 0.0002 to 0.3 mg/kg/day.

No adverse toxicological effects are indicated at the aforementioned dosage ranges.

It is preferred that the 5-HT$_3$ receptor antagonist is administered in the form of a unit dose pharmaceutical composition in which is combined with a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilized by exposure of ethylene oxide before suspending in the sterile vehicle. Advantageously, a surfactant or wetting agent is included in the composition to facilitate uniform distribution of the compound.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

The compositions may contain from 0.1% to 99% by weight, preferably from 10–60% by weight, of the active material, depending on the method of administration.

The present invention also provides the use of a 5-HT$_3$ receptor antagonist, such as compound of formula (I) or (II) or a pharmaceutically acceptable salt thereof in the preparation of a medicament for use in the treatment of cough and/or bronchoconstriction in mammals, including humans. Such treatment may be carried out in the manner as hereinbefore described.

The present invention further provides a pharmaceutical composition for use in the treatment of cough and/or bronchoconstriction which comprises an effective amount of a 5-HT$_3$ receptor antagonist, such as compound of formula (I) or (II), or a pharmaceutically acceptable salt thereof, and a pharmaceutically acceptable carrier. Such compositions may be prepared in the manner as hereinbefore described.

The following clinical tests illustrate the invention.

Compound E6 is the Compound of Example 6 of EP-A-200444, N-(endo-9-methyl-9-azabicyclo-[3.3.]non-3-yl)-1-methyl-indazole-3-carboxamide monohydrochloride.

CLINICAL TESTS

1. Experimental cough in man can be induced by inhalation of capsaicin (the active ingredient of pepper) and coughing occurs in a dose related manner. Administration of compound E6 intravenously at doses up to 60 µg/kg is found to block capsaicin induced cough.

2. Bronchoconstriction in man can be induced by inhalation of capsaicin (the active ingredient of pepper) or by inhalation of sulphur dioxide. Administration of compound E6 intravenously at doses of up to 60 µg/kg is found to block capsaicin or sulphur dioxide induced bronchoconstriction.

I claim:

1. A method of treatment of cough and/or bronchoconstriction in mammals, which method comprises the administration to the mammal in need of such treatment, an effective amount of a 5-HT$_3$ receptor antagonist compound of formula (I) or a pharmaceutically acceptable salt thereof:

$$X—CO—Y—Z— \quad (I)$$

wherein

X is a group of formula (a)

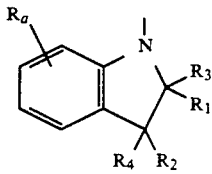

wherein $R_a$ is selected from the group consisting of hydrogen, halogen or hydroxy;

$R_1$ is hydrogen and $R_2$ is hydrogen or $C_{1-4}$ alkyl, or $R_1$ and $R_2$ together are a bond;

$R_3$ is hydrogen or $C_{1-6}$ alkyl;

$R_4$ is hydrogen or $C_{1-6}$ alkyl, and $R_4$ together with $R_2$ maybe $C_{2-7}$ polymethylene when $R_1$ is hydrogen;

Y is NH;

Z is a group of formula (f)

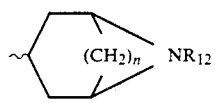

wherein n is 2 or 3; and $R_{12}$ is methyl or ethyl.

2. A method according to claim 1 wherein the compound of formula (I) is BRL 43694A which is N-(endo-9-methyl-9-azabicyclo-[3.3.1]non-3-yl)-1-methyl-indazole-3-carboxamide monohydrochloride.

3. A pharmaceutical composition for use in the treatment of cough and/or bronchoconstriction, which comprises an effective amount of a 5-HT$_3$ receptor antagonist, as defined in claim 1, and a pharmaceutically acceptable carrier.

4. A method of using a 5-HT$_3$ receptor antagonist as defined in claim 1 in the preparation of a medicament, said method including the steps of providing an amount of the 5-HT$_3$ receptor antagonist effective for the treatment of cough and/or bronchoconstriction in mammals, including humans, and admixing said effective amount of the 5-HT$_3$ receptor antagonist with a pharmaceutically acceptable carrier.

5. A method of use as defined by claim 4, wherein said treatment is for cough.

6. A method of use as defined by claim 4, wherein said treatment is for bronchoconstriction.

7. The composition as defined by claim 3 for use in the treatment of cough.

8. The composition as defined by claim 3 for use in the treatment of bronchoconstriction.

* * * * *